US006173715B1

(12) United States Patent
Sinanan et al.

(10) Patent No.: US 6,173,715 B1
(45) Date of Patent: Jan. 16, 2001

(54) MAGNETIC ANATOMICAL MARKER AND METHOD OF USE

(75) Inventors: Mika N. Sinanan, Briar; Christopher P. Somogyi, Clyde Hill; Robert N. Golden, Kirkland; Fred E. Silverstein, Seattle; Andrei J. Gonzales, Lacey, all of WA (US)

(73) Assignee: Lucent Medical Systems, Inc., Kirkland, WA (US)

(*) Notice: Under 35 U.S.C. 154(b), the term of this patent shall be extended for 0 days.

(21) Appl. No.: 09/259,222

(22) Filed: Mar. 1, 1999

(51) Int. Cl.$^7$ .................................................. A61B 19/00
(52) U.S. Cl. ........................... 128/899; 128/898; 600/12; 600/431
(58) Field of Search .............................. 600/12, 407, 409, 600/424, 431; 128/897, 898, 899; 606/151

(56) References Cited

U.S. PATENT DOCUMENTS

| | | | |
|---|---|---|---|
| 3,649,908 | 3/1972 | Brown | 324/43 G |
| 3,757,773 | 9/1973 | Kolin | 128/2.05 F |
| 3,847,157 | 11/1974 | Caillouette et al. | 128/348 |
| 3,916,821 | * 11/1975 | Pies | 116/114 R |
| 3,952,438 | * 4/1976 | Propst et al. | 40/300 |
| 4,063,561 | 12/1977 | McKenna | 128/351 |
| 4,244,362 | 1/1981 | Anderson | 128/200.26 |
| 4,249,536 | 2/1981 | Vega | 128/349 B |
| 4,317,078 | 2/1982 | Weed et al. | 324/208 |
| 4,402,310 | 9/1983 | Kimura | 128/4 |
| 4,608,992 | 9/1986 | Hakim et al. | 128/654 |
| 4,619,247 | 10/1986 | Inoue et al. | 128/6 |
| 4,671,287 | 6/1987 | Fiddian-Green | 128/631 |
| 4,790,809 | 12/1988 | Kuntz | 604/8 |

(List continued on next page.)

FOREIGN PATENT DOCUMENTS

| | | |
|---|---|---|
| 29 03 357 A1 | 7/1980 | (DE) . |
| 40 14 947 A1 | 11/1991 | (DE) . |
| 0 302 001 A1 | 2/1989 | (EP) . |
| 2 102 127 | 1/1983 | (GB) . |
| 02 021 290 | 1/1990 | (JP) . |
| 93 04628 | 3/1993 | (WO) . |
| 9608999 A1 | 3/1996 | (WO) . |

OTHER PUBLICATIONS

James, A.H., "Duodenal Intubation with Magnet–Tipped Tubes," *The Lancet*: 209–210, Jan. 27, 1951.
Wenger et al., "Magnet–Tipped Tubes for Studies of the Stomach and Duodenum," *Digestive Diseases*, vol. 15, No. 4: 383–393, Apr. 1970.

(List continued on next page.)

Primary Examiner—Cary O'Connor
Assistant Examiner—Charles Marmor, II
(74) Attorney, Agent, or Firm—Michael J. Donohue; Seed IP Law Group PLLC

(57) ABSTRACT

An anatomical marker uses a permanent magnet to indicate a selected location within a patient. The magnet is enclosed within a non-degradable envelope and is coupled to a retention member that is preferably manufactured from a biodegradable material, such as a polyglucuronic acid based material. The retention member may include one or more barbs to retain the anatomical marker in the selected location. An insertion tool, usable with an endoscope, can insert the anatomical marker. A retention magnet is fixedly attached to the insertion tool and holds the anatomical marker in place due to the attractive magnetic forces between the retention magnet and the marker magnet in the non-biodegradable envelope. When the anatomical marker is securely fastened at the selected location in the patient, the forces exerted by the patient's body on the retention member exceed the attractive magnetic forces between the retention magnet and the magnet in the envelope, thus causing the anatomical marker to be released from the insertion tool. The location of the magnet may be subsequently detected using a magnetic detector system.

26 Claims, 2 Drawing Sheets

U.S. PATENT DOCUMENTS

| | | | |
|---|---|---|---|
| 4,809,713 | 3/1989 | Grayzel | 128/785 |
| 4,913,139 | 4/1990 | Ballew | 128/200.11 |
| 4,943,770 | 7/1990 | Ashley-Rollman et al. | 324/207.17 |
| 5,005,592 | 4/1991 | Cartmell | 128/899 |
| 5,042,486 | 8/1991 | Pfeiler et al. | 128/653 R |
| 5,099,845 | 3/1992 | Besz et al. | 128/653.1 |
| 5,134,370 | 7/1992 | Jefferts et al. | 324/247 |
| 5,257,636 | 11/1993 | White | 128/897 |
| 5,325,873 | 7/1994 | Hirschi et al. | 128/899 |
| 5,381,095 | 1/1995 | Andrews | 324/326 |
| 5,425,367 | 6/1995 | Shapiro et al. | 128/653.1 |
| 5,425,382 | 6/1995 | Golden et al. | 128/899 |
| 5,429,132 | 7/1995 | Guy et al. | 128/653.1 |
| 5,456,718 | 10/1995 | Szymaitis | 623/11 |
| 5,558,091 | 9/1996 | Acker et al. | 128/653.1 |
| 5,622,169 | 4/1997 | Golden et al. | 128/653.1 |
| 5,624,430 | 4/1997 | Eton et al. | 606/1 |
| 5,645,065 | 7/1997 | Shapiro et al. | 128/653.1 |
| 5,799,099 * | 8/1998 | Wang et al. | 382/131 |
| 5,833,608 * | 11/1998 | Acker | 600/409 |
| 5,853,366 * | 12/1998 | Dowlatshahi | 600/434 |
| 5,873,822 * | 2/1999 | Ferre et al. | 600/407 |
| 5,902,310 * | 5/1999 | Foerster et al. | 606/142 |
| 5,906,579 * | 5/1999 | Vander Salm et al. | 600/424 |
| 5,941,890 * | 8/1999 | Voegele et al. | 606/151 |
| 6,026,818 * | 2/2000 | Blair et al. | 128/899 |

OTHER PUBLICATIONS

Gaston et al., "External Magnetic Guidance of Endovascular Catheters with a Superconducting Magnet: Preliminary Trials," *Journal of Neuroradiology* 15(2): 137–147, 1988.

Ram et al., "Heart Catheterization in a Neonate by Interacting Magnetic Fields: A New and Simple Method of Catheter Guidance," *Catheterization and Cardiovascular Diagnosis* 22(4): 317–319, Apr. 1991.

Williams et al. Abstract, "The Localisation of Enteral Tubes Using a Novel Non–Radiological Technique ("Cathlocator"), " *British Society of Gastroenterology*, Mar. 1992.

Weitschies et al., "Magnetic Markers as a Noninvasive Tool to Monitor Gastrointestinal Transit," *IEEE Transactions on Biomedical Engineering*, 41(2): 192–195, Feb. 1994.

* cited by examiner

MAGNETIC ANATOMICAL MARKER AND METHOD OF USE

TECHNICAL FIELD

The present invention is related generally to an anatomical marker and, more particularly, to a magnetic anatomical marker and method of use.

BACKGROUND OF THE INVENTION

Surgical procedures, such as colorectal resection or polyp removal are often preceded by preoperative endoscopic evaluation. The purpose of such preoperative procedures is to identify malignant or potentially malignant tissue for subsequent removal. For example, a colonoscopy is performed to locate potentially malignant polyps or tissue on the interior bowel wall. During the colonoscopy a biopsy may be performed to remove tissue or polyps for histological evaluation. If malignancy is confirmed, surgical resection of the diseased portion of the colon is required. However, the colonic mucosa heals quickly after removal of the polyp, thus making it difficult to identify the former location of the polyp. In addition, the surgeon typically performs a colon resection by visualizing the exterior of the bowel, and the location of the interior diseased tissue is often not evident from the exterior of the bowel.

There are known techniques for marking areas of the colon for subsequent removal. The most widely known marking technique utilizes India ink injected via a needle passed through the endoscope as a form of "tattoo" to mark the area of the colon. However, there are many known drawbacks to the use of India ink. Migration of the India ink often makes precise location of colon tissue difficult. Furthermore, the colon histology may be altered or obscured by the ink. Altered or obscured colon histology may result in misdiagnoses of malignant colon tissues by a pathologist. In addition, a number of complications are associated with India ink, including necrosis, edema and perforation of the bowel wall.

Estimates of colon lesion location based on interior endoscopic examination are often incorrect or inaccurate due to the contractile and pliant nature of the colon. Other techniques of locating colon lesions, such as endoscopic clips, barium radiography and fluoroscopy require expensive equipment and radiation exposure.

Therefore, it can be appreciated that there is a significant need for a non-radiographic marking system to accurately mark the location of a colon lesion without altering the colon histology. The present invention provides this and other advantages as will be apparent from the following description and accompanying figures.

SUMMARY OF THE INVENTION

The present invention is embodied in a system and method for use of magnetic markers to indicate anatomical locations. The magnetic marker system comprises a central portion having first and second ends and a magnetic element associated with the first end. The magnetic element is detectable from a location at some distance from the magnetic marker. A retainer mechanism associated with the second end retains the magnetic element in a selected location.

In one embodiment, the first end may comprise a magnetic material with the magnetic element being a magnetized first end. The magnetic material may also be coupled to the first end. In one embodiment, the magnetic element may be coupled to the first end by a biodegradable material.

The retainer mechanism may comprise barbs to provide retention of the magnetic element in the selected location. In one embodiment, the barbed end is manufactured from a biodegradable material that will break down over time thus releasing the magnetic element.

The magnetic marker may be inserted within the interior portion of an anatomical structure, such as a bowel. The system may further include a magnetic detector system operable from a location external to the anatomical structure to detect the location of the magnetic element within the anatomical structure.

DETAILED DESCRIPTION OF THE INVENTION

The present invention is directed to an anatomical marker system using permanent magnets, which may be detected from a location at some distance from the anatomical marker. The system uses a permanent magnet as the signal source. The static magnetic field generated by a permanent magnet can be readily measured from a distance of several centimeters. The static magnetic field is not attenuated or affected by intervening air or tissue or by the presence of blood or other body fluids. In addition, there is no energy deposited in the tissue by the static magnetic field, nor has there been shown to be any health affect on tissue by a static magnetic field. As will be described in further detail, the detector system is a passive magnetic field sensor that adds no risk to the patient.

Figure 1:
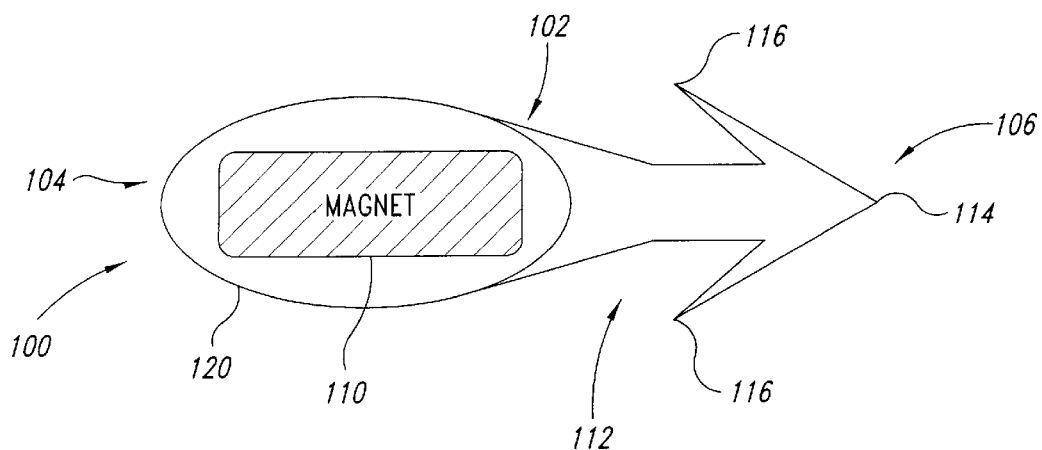
FIG. 1 is a top plan view of the magnetic surgical tag of the present invention.

The present invention is embodied in an anatomical marker 100 illustrated in FIG. 1. The anatomical marker 100 comprises a central portion 102 having a first end 104 and a second end 106. A permanent magnet 110 is associated with the first end 104 to generate the static magnetic field, as described above. Additional details regarding the detection of the magnet 110 are provided below. The second end 106 includes a retainer member 112 to retain the anatomical marker 100 at a fixed location within the patient.

In an exemplary embodiment, the retainer member 112 includes a spear point 114 to penetrate the patient's tissue and one or more barbs 116 to retain the anatomical marker 100 within the patient's tissue at a location selected by the surgeon. As those skilled in the art can appreciate, the retainer member 112 may comprise other satisfactory shapes to retain the anatomical marker 100 within the patient tissue. For example, the retainer member 112 may comprise a hook, a surgical staple, or the like to retain the anatomical marker 100 at the selected location in the patient. Alternatively, the retainer member 112 may comprise surgical glue to retain the anatomical marker 100 at the desired location. In yet another alternative embodiment, the surgeon may suture the anatomical marker 100 at the desired location within the patient. The present invention is not limited by the specific structure or mode of operation of the retainer member 112.

In an exemplary embodiment, the retainer member 112 is formed from a biodegradable material that will slowly dissolve over time and release the magnet 110. For example, the retainer member 112 can be formed from a polyglucuronic acid based degradable material that is molded into the desired shape. As those skilled in the art will appreciate, a polyglucuronic acid based material will biodegrade in the body over a period of time, thus releasing the magnet 110. In this embodiment, the magnet 110 is enclosed in an envelope 120 that is manufactured from a non-degradable material. Thus, the magnet 110 is protected from the bodily fluids by the non-degradable envelope 120. When used in combination with the degradable retainer member 112, the anatomical marker 100 provides secure retention of the magnet 110 at the desired anatomical location, such as the interior wall of the intestines, for a period of time. After the retainer member 112 degrades, the magnet contained within the non-degradable envelope 120 is released and expelled from the body along with fecal material. To permit easy passage of the magnet 110, the envelope 120 has smooth outer walls. Similarly, the other forms of the retainer member 112, such as a hook, surgical staple, or sutures may also be manufactured from a degradable material so that the magnet 110 contained within the non-degradable envelope 120 is released after a period of time.

Those skilled in the art will appreciate that the presence of the magnet 110 may be a hazard if the patient were placed in the presence of a strong magnet field, such as is typically used in magnetic resonance imaging (MRI). The MRI magnet may cause potential movement of the anatomical marker 100. Thus, the patient should not be exposed to such powerful magnetic fields while the anatomical marker 100 is present within the patient. However, with the degradable retainer member 112, the magnet 110 is held in place only a relatively short period of time. A polyglucuronic acid based degradable material has a half-life of approximately 4 to 6 weeks, which allows adequate time to place patient into a surgical schedule, and exceeds the time that injections of India ink are effective. Thus, the magnet 110 and the non-degradable envelope 120 will typically detach and pass after approximately 4 to 6 weeks. A magnetic detector system, described below, can determine whether the magnet 110 is still present in the patient.

In an exemplary embodiment, the magnet 110 is a commercial product using high residual induction magnet types such as alnico, samarium cobalt (SmCo) or Neodymium Iron Boron (NdFeB). These magnet types provide a large magnetic field strength for their size. Table 1 below indicates the magnetic field (in Gauss) as a function of distance of a commercially available NdFeB rod magnet having a 2 mm diameter and a 5 mm length and a strength grade of 35 H:

TABLE 1

| Distance (mm) | Field (Gauss) |
| --- | --- |
| 5 | 89 |
| 6 | 58 |
| 7 | 41 |
| 8 | 29 |
| 9 | 22 |
| 10 | 17 |
| 5 | 6 |
| 20 | 3 |
| 30 | 1 |
| 40 | less than 1 |

Figure 2:
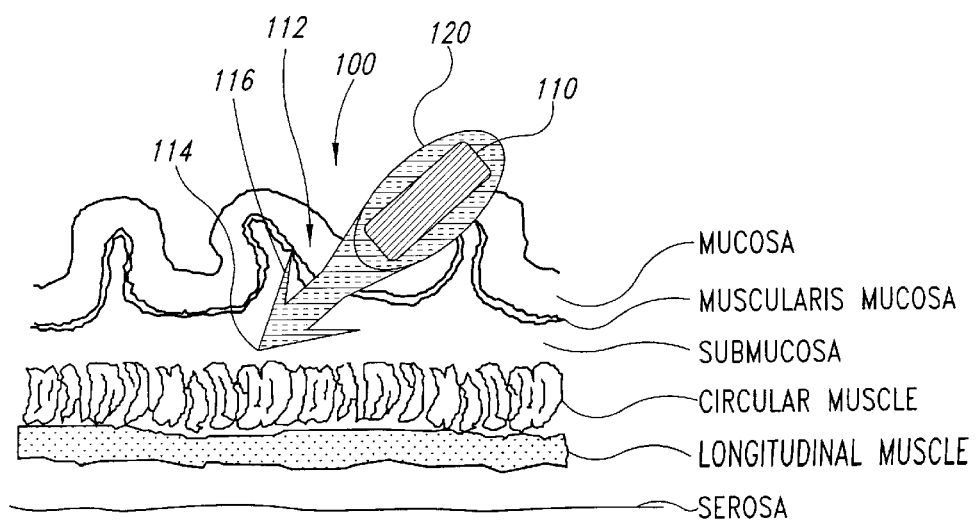
FIG. 2 illustrates the magnetic surgical tag of FIG. 1 inserted within the wall of a colon.

Proper use of the anatomical marker 100 requires that it be retained in the selected location. As discussed above, the retainer member 112 serves to retain the magnet 110 at the desired location. FIG. 2 illustrates the insertion of the anatomical marker 100 within a portion of the colon. The portion of the colon illustrated in FIG. 2 is shown in a longitudinal cross-section and includes labels illustrating the various layers of the colon. In an exemplary embodiment, the spearpoint 114 and barbs 116 penetrates the mucosa and muscularis mucosa. The barbs 116 serve to securely anchor the retainer member 112 within the submucosa. The muscularis mucosa is a strong layer of the bowel wall and should provide sufficient strength to retain the anatomical marker 100 at the selected location. It is undesirable to completely penetrate the wall of the colon because of potential complications, such as bleeding and necrosis. Penetration into the submucosa minimizes the wall penetration and helps avoid these potential complications.

Figure 3:
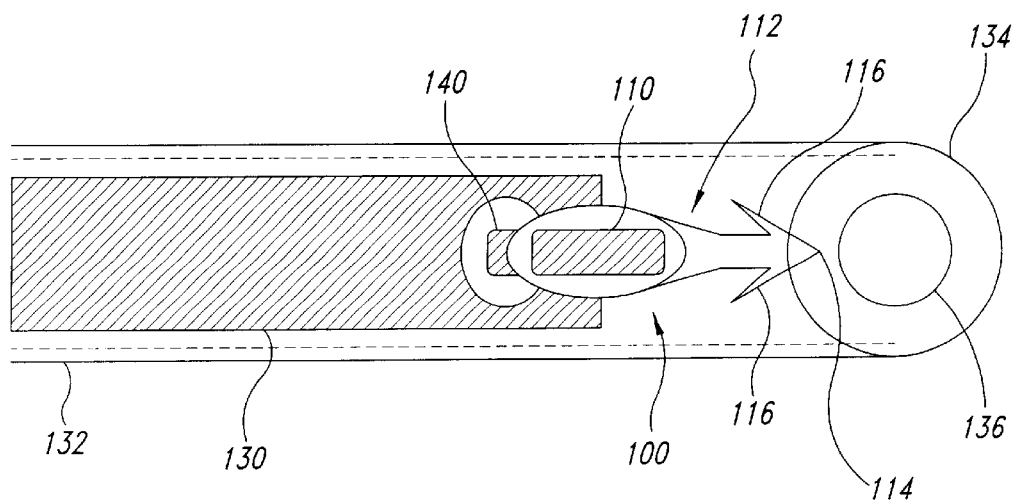
FIG. 3 is a plan view of an apparatus to introduce the magnetic surgical marker of FIG. 1.

The anatomical marker 100 can be securely inserted using a tag insertion tool 130, illustrated in FIG. 3. The insertion tool 130 is sized to fit through an instrument port 132 of an endoscope. The instrument port 132 has a distal catheter tip 134 containing an aperture 136. The aperture 136 is sized to permit passage of the anatomical marker 100.

The insertion tool 130 is calibrated to release the anatomical marker 100 only if it has been anchored securely. A magnetic force mechanism is used to measure the tensile strength of the anatomical marker implanted in the submucosa of the bowel wall (see FIG. 2). The insertion tool 130 includes an introducer magnet 140, which is fixedly attached to a terminal portion of the insertion tool 130. The introducer magnet 140 has a magnetic field strength and orientation such that it magnetically couples with and retains the magnet 110 and anatomical marker 100 by use of attractive magnetic forces. The strength of magnetic coupling between the magnet 110 and the introducer magnet 140 is calibrated to release the magnetic anatomical marker 100 only if the retainer member 112 has been securely anchored to the bowel wall.

The user positions the catheter tip 134 at the desired location of the bowel wall and advances the insertion tool 130 within the instrument port 132 until the retainer member 112 extends through the aperture 136 and penetrates into the submucosa (see FIG. 2). The user then retracts the insertion tool 130. If the retainer member 112 is not properly secured within the submucosa, the magnetic coupling between the introducer magnet 140 and the magnet 110 will cause the anatomical marker 100 to remain attached to the insertion tool 130. However, if the retainer member 112 is securely anchored within the submucosa, the mechanical forces required to pull the anatomical marker 100 loose from the bowel wall exceed the attractive magnetic forces between the introducer magnet 140 and the magnet 110. In this case, the anatomical marker 100 will break free from the magnet affects of the introducer magnet 140 and the anatomical marker will be retained within the bowel wall at the selected location.

Figure 4:
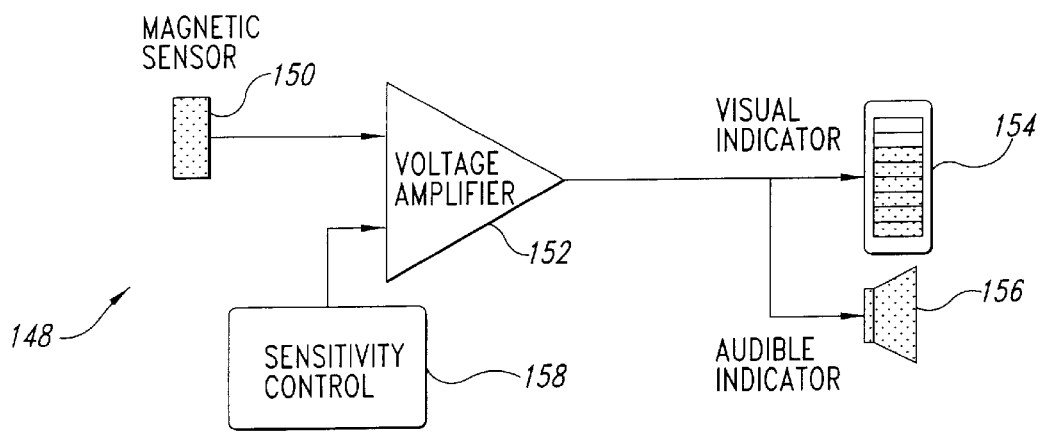
FIG. 4 is a functional block diagram of a detector system used to detect the location of the surgical magnetic marker.

Once in place, the anatomical marker 100 may be readily detected using a variety of different magnetic detector technologies. One such detector is illustrated in FIG. 4 where a low-cost magnetic detector system 148 uses a single magnetic sensor 150 to detect the presence of the magnet 110. In an exemplary embodiment, the magnetic sensor 150 may be a single Hall-effect sensor, which is commercially available and relatively inexpensive. With a strong magnetic field, a single Hall-effect sensor can accurately detect and locate the anatomical marker. As indicated in Table 1, a NdFeB magnet can produce several Gauss of magnetic field strength at a distance of 10–15 mm. Thus, a single magnetic sensor 150 provides a low cost detector system. The magnetic sensor 150 generates a voltage that is dependent on the strength of the magnetic field. The output of the magnetic sensor is coupled to a voltage amplifier 152 whose output is connected to a visual indicator 154 and/or an audible indicator 156. The visual indicator 154 may be in the form of a LED bar graph indicator in which the number of lighted segments corresponds to the strength of the magnetic field. Similarly, the audible indicator 156 may generate an audible tone whose frequency or amplitude increases in relation to the magnetic field detected by the magnetic sensor 150. A sensitivity control 158 can adjust the gain of the amplifier 152 in a known manner.

In operation, the magnetic detector system 148 can determine the location of one or more anatomical markers 100. The magnetic detector system 148 is particularly useful in detecting anatomical markers 100 from a location outside an anatomical structure. For example, the anatomical marker 100 may be inserted in the interior portion of the colon using an endoscope, as described above. In a subsequent surgical procedure, such as laparoscopic surgery, the magnetic detector system 148 is used on the external portion of the colon or other anatomical structure to locate the anatomical marker 100. Thus, the anatomical marker 100 on the internal portion of an anatomical structure can be detected from a location external the anatomical structure.

The simplified detector system illustrated in FIG. 4 is adequate for a strong magnet at close range, even in the presence of a background magnetic field generated by the Earth, which may be as high as 600 milliGauss (mG). With a magnet such as the NdFeB magnet described with respect to Table 1, the Earth's magnetic field is not a significant factor.

However, for some applications, the locating distance may be large or a smaller magnet may be required for anatomical reasons. In this case, the magnetic field may be very weak at anatomically useful distances and thus require a more sensitive magnetic detector. Such a detector is known in the art and described, for example, in U.S. Pat. No. 5,425,382, and U.S. Pat. No. 5,622,169. In addition, a magnetic detector system is described in U.S. patent application Ser. No. 08/852,940, filed on May 8, 1997, which is incorporated herein by reference in its entirety. Similar technology is described in U.S. patent application Ser. No. 09/075,280, filed on May 8, 1998, and published as PCT Publication No. WO 98/49938, on Nov. 12, 1998, which is also incorporated herein by reference in its entirety. In those patents, applications, and publications, multiple magnetic sensors are used to detect and locate the anatomical marker 100. Multiple magnetic sensors may be arranged to generate a differential magnetic signal or a magnetic gradient. The magnetic sensors may be Hall-effect sensors or magneto-resistive sensors. Currently available magneto-resistive sensors can detect magnetic field strength differences on the order of 1.0 mG. Such a differential magnetic sensor is capable of detecting a much lower magnetic field strength even in the presence of the Earth's magnetic field. The detectors described in the cited references are more expensive than the simple detector of FIG. 4 since the sensors and associated electronics are more costly. However, those skilled in the art will appreciate that a variety of detector technologies may be satisfactorily used to detect the location of the anatomical marker 100.

The use of the anatomical marker 100 to mark polyps or tumors within the gastrointestinal tract for surgical localization and removal has been described above. Once the site of a malignant polyp or tissue has been marked with the anatomical marker 100, a laparoscopic surgical procedure may be performed. The abdomen is insufflated and the colon visualized. The location of the anatomical marker may be accurately determined with the magnetic field detector. Using either known internal or external techniques, the bowel is opened and the polyp is resected. If malignant, a section of the bowel may be removed as well. If benign, only the polyp is removed and the colon closed.

Alternatively, in a non-laparoscopic procedure, the abdomen may be surgically opened and the colon palpated. If the lesion or the anatomical marker 100 cannot be felt, the colon may be scanned using the magnetic detector system 148 to accurately determine the location of the anatomical marker. This procedure avoids unnecessary immobilization of the colon. If multiple lesions are present and marked, each can be localized, marked externally, and a plan for dealing with multiple lesions can then be formulated.

In another example, a patient with a history of colon cancer may have a small lung nodule detected at the time of a chest x-ray and confirmed by a chest computerized tomography (CT). If the mass is biopsied and cancer confirmed, the nodule may be marked with the anatomical marker 100 on the surface of the lung or in the lung that can later be located visually or magnetically using the magnetic detector system 148. At the time of thoracic lung resection, the lesion, which is notoriously hard to detect by appearance, may be precisely located by the anatomical marker 100 with or without the magnetic detector system 148. The resection is carried out and the marker and lesion evaluated to make sure that the nodule is completely removed. In yet another example, during colonoscopy, the gastroenterologist may find a rectal cancer. The cancer is typically visualized during a first step of the operation and a suitable margin is chosen distally. That is, an area surrounding the cancerous tissue is identified for removal. The anatomical marker 100 may be placed at the site of the cancerous tissue and a predetermined area surrounding the anatomical marker removed. Alternatively, two or more anatomical markers 100 may be placed at the resection point surrounding the cancerous tissue. During dissection of the rectum, the anatomical marker 100 is used to confirm an adequate distal margin before resection using a stapling device. In such an operation, it is important to assure that the resection staple line does not include the anatomical marker since that might compromise the closure of the resection. Use of the anatomical marker 100 is an efficient way of avoiding the use of a scope and the necessity of changing gloves or gown when coming back to the abdominal surgical field.

The benefits of accurate close range detection of the anatomical marker 100 are even more pronounced when used with a laparoscopically low anterior resection since there are not any currently recognized procedures to replace the lost palpation of the specimen. That is, a surgeon can palpate the specimen to detect cancerous lumps during open abdominal surgery, but such palpation is not possible with laparoscopic surgery. However, in one embodiment, the magnetic detector system 148 can be attached to a laparoscopic tool and inserted within the patient's abdomen to detect one or more anatomical markers 100 that have been previously inserted using the endoscopic procedure described above.

In yet another example, the anatomical marker may be used during rectal mucosectomy prior to formation of an ileoanal anastomosis for treatment of ulcerative colitis or familial polyposis wherein the proximal line of resection may be marked with one or more anatomical markers 100. Once the intraoperative portion of the operation has begun, the colon is dissected down to the level of the anatomical markers before transecting the rectum. This procedure has the benefit of avoiding intraoperative endoscopy. If intraoperative endoscopy is required to visualize the line of resection, the surgical procedure takes more time since the surgeon must change gloves and gown and reprepare the surgical area following the endoscopic portion of the procedure. As those skilled in the art can appreciate, the use of anatomical markers 100 may reduce the surgical time 10 or more minutes. At a cost of 17–23 dollars per minute for an operating room, such a savings becomes significant.

It is to be understood that even though various embodiments and advantages of the present invention have been set forth in the foregoing description, the above disclosure is illustrative only, and changes may be made in detail, yet remain within the broad principles of the invention. Therefore, the present invention is to be limited only by the appended claims.

What is claimed is:

1. A magnetic marker system for anatomical location, comprising:
   a central portion having first and second ends;
   a magnetic element associated with the first end; and
   a retainer member associated with the second end for retention in a selected location wherein the retainer member is manufactured from a biodegradable material.

2. The system of claim 1 wherein the first end comprises a magnetic material and the magnetic element is the magnetized first end.

3. The system of claim 1 wherein the magnetic element comprises a magnet coupled to the first end.

4. The system of claim 3 wherein the magnet is a rare-earth magnet type.

5. The system of claim 1 wherein the retainer member comprises a barbed end to provide the retention in the selected location.

6. The system of claim 1, wherein the retainer member is adapted for insertion in an internal portion of an anatomical structure, the system further comprising a magnetic detector operable from a location external the anatomical structure to detect the location of the magnetic element within the anatomical structure.

7. The system of claim 6 wherein the magnetic detector comprises a first magnetic sensor element.

8. The system of claim 6 wherein the magnetic detector comprises a Hall-effect magnetic sensor element.

9. A magnetic marker system for anatomical location, comprising:
   a central portion having first and second ends;
   a magnet coupled to the first end by a biodegradable material; and
   a retainer member associated with the second end for retention in a selected location.

10. A magnetic marker system for anatomical location, comprising:
    a central portion having first and second ends;
    a magnetic element associated with the first end; and
    a retainer member associated with the second end and having a barbed end for retention in a selected location wherein the barbed end is manufactured from a biodegradable material.

11. A magnetic marker system for anatomical location, comprising:
    an envelope sized for insertion within a patient;
    a magnetic element contained within the envelope; and
    a retainer member coupled to the envelope to retain the envelope in a selected location wherein the retainer member is manufactured from a biodegradable material.

12. The system of claim 11 wherein the magnetic element is a rare-earth type magnet.

13. The system of claim 11 wherein the envelope is manufactured from a non-degradable material.

14. The system of claim 11 wherein the retainer member is manufactured from a polyglucuronic acid based material.

15. The system of claim 11 wherein the retainer member comprises a barbed end to retain the envelope in the selected location.

16. The system of claim 15 wherein the barbed end is manufactured from a biodegradable material.

17. The system of claim 11, further comprising a magnetic detector operable to detect the location of the magnetic element within the patient.

18. The system of claim 17 wherein the magnetic detector comprises a Hall-effect magnetic sensor element.

19. A magnetic marker system for anatomical location, comprising:
    an envelope sized for insertion within a patient;
    a magnetic element contained within the envelope;
    a retainer member coupled to the envelope to retain the envelope in a selected location;
    an insertion tool sized to pass through an instrument port of an endoscope; and
    an insertion magnet fixedly attached to a terminal end of the insertion tool, the insertion magnet having a magnetic orientation to magnetically attract and retain the magnetic element with a predetermined magnetic attraction force until the retainer member is firmly attached to the selected location with a retention force that exceeds the predetermined magnetic attraction force.

20. A method of using a magnetic marker for anatomical location, the method comprising:
    inserting a magnetic marker device into a patient, the magnetic marker device comprising a magnetic element and a retainer member manufactured from a biodegradable material; and
    affixing the magnetic marker device at a selected anatomical location within the patient by affixing the retainer member to the selected anatomical location.

21. The method of claim 20 wherein the magnetic element is a rare-earth type magnet.

22. The method of claim 20, further comprising placing the magnetic element in an envelope manufactured from a non-degradable material.

23. The method of claim 20 wherein affixing the magnetic marker device comprises affixing the magnetic marker device to the selected anatomical location using a polyglucuronic acid based material.

24. The method of claim 20 wherein the magnetic marker device comprises a barbed end and affixing the magnetic marker device comprises inserting the barbed end of the magnetic marker device at the selected anatomical location.

25. The method of claim 20 wherein the selected anatomical location is an interior portion of an anatomical structure the method further comprising detecting the magnetic field generated by the magnetic element from a location external the anatomical structure.

26. A method of using a magnetic marker for anatomical location, the method comprising:
    inserting a magnetic marker device into a patient, the magnetic marker device comprising a magnetic element;
    affixing the magnetic marker device at a selected anatomical location within the patient, wherein affixing the magnetic marker device further comprises:
    placing an insertion magnet, fixedly attached to a terminal end of an insertion tool, in proximity with the magnetic marker device, the insertion magnet having a magnetic orientation to magnetically attract and retain the magnetic element with a predetermined magnetic attraction force;
    inserting the insertion tool into the patient;
    affixing the magnetic marker assembly to the selected location; and
    withdrawing the insertion tool and, if the magnetic marker device is attached to the selected location with a retention force that exceeds the predetermined magnetic attraction force, separating the magnetic marker device from the insertion tool.

* * * * *

UNITED STATES PATENT AND TRADEMARK OFFICE
CERTIFICATE OF CORRECTION

PATENT NO. : 6,173,715 B1  
DATED : January 16, 2001  
INVENTOR(S) : Sinanan et al.

Page 1 of 1

It is certified that error appears in the above-identified patent and that said Letters Patent is hereby corrected as shown below:

<u>Title page,</u>  
Item [56], References Cited, should read:
-- 3,528,402   9/1970  Abramowitz ................128/2  
   4,247,406   1/1981  Widder et al. ................252/62.53  
   5,377,678   1/1995  Dumoulin et al. ............28/653.1  
   9608208A1   3/1996  (WO)  
   97/37616    10/1997 (WO)  
   0 894 503 A2  2/1999  (EP) --.

Signed and Sealed this

Eighteenth Day of December, 2001

Attest:

Attesting Officer

JAMES E. ROGAN  
*Director of the United States Patent and Trademark Office*